(12) United States Patent
Palumbo

(10) Patent No.: US 10,844,545 B2
(45) Date of Patent: Nov. 24, 2020

(54) SUPERABSORBENT MATERIAL SAT (SUPER ABSORBENT TISSUE)

(71) Applicant: Gianfranco Palumbo, Pescara (IT)

(72) Inventor: Gianfranco Palumbo, Pescara (IT)

( * ) Notice: Subject to any disclaimer, the term of this patent is extended or adjusted under 35 U.S.C. 154(b) by 113 days.

(21) Appl. No.: 16/069,743

(22) PCT Filed: Jan. 20, 2016

(86) PCT No.: PCT/EP2016/051089
§ 371 (c)(1),
(2) Date: Jul. 12, 2018

(87) PCT Pub. No.: WO2016/120130
PCT Pub. Date: Aug. 4, 2016

(65) Prior Publication Data
US 2019/0017225 A1 Jan. 17, 2019

(30) Foreign Application Priority Data
Jan. 30, 2015 (IT) .............................. GE2015A0013

(51) Int. Cl.
| | |
|---|---|
| *D21H 21/22* | (2006.01) |
| *B01J 20/26* | (2006.01) |
| *B01J 20/28* | (2006.01) |
| *B01J 20/30* | (2006.01) |
| *B01J 20/32* | (2006.01) |
| *D21H 21/20* | (2006.01) |
| *D21H 17/43* | (2006.01) |
| *D21H 17/45* | (2006.01) |
| *D21H 17/55* | (2006.01) |
| *D21H 19/12* | (2006.01) |
| *D21H 27/00* | (2006.01) |
| *D21H 27/10* | (2006.01) |
| *A61L 15/60* | (2006.01) |

(52) U.S. Cl.
CPC .............. *D21H 21/22* (2013.01); *A61L 15/60* (2013.01); *B01J 20/261* (2013.01); *B01J 20/28023* (2013.01); *B01J 20/28028* (2013.01); *B01J 20/3085* (2013.01); *B01J 20/327* (2013.01); *B01J 20/3225* (2013.01); *B01J 20/3293* (2013.01); *D21H 17/43* (2013.01); *D21H 17/45* (2013.01); *D21H 17/55* (2013.01); *D21H 19/12* (2013.01); *D21H 21/20* (2013.01); *D21H 27/002* (2013.01); *D21H 27/10* (2013.01)

(58) Field of Classification Search
None
See application file for complete search history.

(56) References Cited

U.S. PATENT DOCUMENTS

| | | | |
|---|---|---|---|
| 5,516,585 A | 5/1996 | Young, Sr. et al. | |
| 5,607,550 A | 3/1997 | Akers | |
| 5,693,707 A * | 12/1997 | Cheng | A61L 15/24 524/556 |
| 5,795,439 A | 8/1998 | Euripides et al. | |
| 5,997,690 A | 12/1999 | Woodrum | |
| 6,056,854 A | 5/2000 | Woodrum | |
| 6,979,386 B1 | 12/2005 | Wallajapet et al. | |
| 2002/0007166 A1 * | 1/2002 | Mitchell | D21H 21/22 604/368 |
| 2002/0007169 A1 | 1/2002 | Graef et al. | |
| 2002/0058740 A1 | 5/2002 | Lorah et al. | |
| 2003/0127202 A1 | 7/2003 | Reinheimer et al. | |
| 2003/0149413 A1 | 8/2003 | Mehawej | |
| 2005/0224200 A1 | 10/2005 | Bouchard et al. | |
| 2006/0173097 A1 | 8/2006 | Ahmed et al. | |
| 2008/0115898 A1 | 5/2008 | Gelli et al. | |
| 2010/0099781 A1 | 4/2010 | Tian et al. | |

FOREIGN PATENT DOCUMENTS

| | | |
|---|---|---|
| EP | 0359615 A1 | 3/1990 |
| EP | 0437816 A1 | 7/1991 |
| EP | 0702031 A2 | 3/1996 |
| JP | S61-113900 | 5/1986 |
| JP | H11-172598 | 6/1999 |
| JP | H11-189997 | 7/1999 |
| JP | 2004-509986 | 4/2004 |
| JP | 2007-510804 | 4/2007 |
| JP | 2014-070289 | 4/2014 |
| RU | 2518063 C2 | 6/2014 |
| WO | 01/00259 | 1/2001 |
| WO | 02/100032 A1 | 12/2002 |
| WO | 03/092757 | 11/2003 |
| WO | 2005/098134 A1 | 10/2005 |

OTHER PUBLICATIONS

International Search Report and Written Opinion dated May 3, 2016 by the European Patent Office as International Searching Authority of counterpart international patent application No. PCT/EP2016/051089.

* cited by examiner

*Primary Examiner* — Dennis R Cordray
(74) *Attorney, Agent, or Firm* — Stradley Ronon Stevens & Young, LLP

(57) ABSTRACT

A method for wet production of a superabsorbent material. The method comprises forming an aqueous saline solution with a concentration of 0.01-4.5 N of ionic salt and a pH from 0 to 6.0 or from 8.0 to 14.0 by the addition of a strong acid or strong base; dispersing in the saline solution a water superabsorbent polymer (SAP); creating a first web by stratification and deposition under vacuum suction onto a mesh screen belt deposition section of the SAP dispersion; washing the web with a basic solution (or with an acidic solution) up to the desired level of neutralization of the acidity (or basicity) for SAP dispersions in acidic (or basic) saline solutions; washing the web with water and suction; and drying the web. The relationship between pH and salt concentration causes a water absorption in the SAP equal to or less than about 30.00 $g_{H2O}/g_{SAP}$.

27 Claims, 2 Drawing Sheets

SUPERABSORBENT MATERIAL SAT (SUPER ABSORBENT TISSUE)

RELATED APPLICATION

This application is a U.S. national phase application of International Patent Application No. PCT/EP2016/051089 filed on Jan. 20, 2016 and published as International Publication No. WO 2016/120130 on Aug. 4, 2016.

FIELD OF THE INVENTION

The present invention is directed to a method for the wet production of a superabsorbent material. Specifically, the method is directed to the production of a web or a multi-web containing a water superabsorbent polymer (SAP) selected among the polymers comprising at least one acidic resin not completely neutralized or comprising at least one basic resin not completely neutralized, or a multi-web of SAP with acidic resin alternate to SAP with basic resin not completely neutralized.

BACKGROUND

"Tissue Paper", is generally used for absorbing liquids, in the form of products such as absorbent kitchen towel rolls, disposable facial tissues, packaging absorbent mats, toilet paper, table napkins, female sanitary towels, diapers for babies or diapers for incontinent adults, etc. The basic properties of these materials are the absorption, the specific weight, the thickness, the specific volume, the brightness, the tensile strength, the appearance and comfort, such as the roughness and/or softness.

Tissue papers are mainly produced with a wet-laid method on papermaking plants, as well as some kinds of wet-laid nonwovens or NW obtained in similar plants, but also using other fibers, beside the cellulose ones, with or without chemical binders.

Some qualitative improvements of said tissue papers as well as wet-laid NW, are obtained through both mechanical, among which mention is made of creeping and embossing, and heat treatments, mainly for the drying treatment Through a Air Dried (TAD), which improve the properties of softness, bulkiness and absorption ability thereof. The latter feature is crucial for using such materials. The absorption limit of the tissue paper is from about 10 to 16 grams of water per gram of material, as free absorption, namely by immersion and dripping and without imparting pressure.

Thus, in order to enhance the ability of liquid absorption, as well as optimize the consumptions and energy costs, since the production of tissue papers and wet-laid NW uses high amounts of energy, innovations concerning both the materials and production technologies used are required.

Furthermore, since the products in which said materials are used are of mono- or limited-use type, a further aspect to be considered is the manufacture of products with novel forms of eco-sustainable disposability.

Therefore, it is very interesting for these materials the possibility to combine other materials with absorption ability of one or two orders of magnitude greater than that of cellulose fibers, such as the Superabsorbent Polymers (SAP), equal or similar to those being used, for example in diapers for babies or incontinent adults, which can exhibit free absorptions of 140-150 g/g or greater.

One of the main problems occurring when combining the SAP in the blend of the papermaking plant, as well as of the wet-laid nonwoven plant, is that the SAP, by absorbing and gelatinizing big amounts of water, even at very low concentrations, causes a practical inability of the plant to function due to the intrinsic formation of bulky gelatinous lumps. Accordingly, the big mass of water absorbed in the gelatinized portion of the SAP, would lead to enormous problems, both technical, as regards operating times and machinery rate, and economical, mainly as drying costs, which prevents its use in the present state of the art.

For this purpose, several attempts were made, but with poor practical results. One of the few attempts with remarkable results, even if produced off-line, is described in the patent WO2005098134 A1 wherein the SAP particles, in the form of powder with variable granulometry, are placed between two layers of tissue paper, in the form of laminate and thus non-entrapped among the cellulose fibers. Therefore, it results that the material is prone to delamination, in particular after imbibition with water, allowing to combine limited amounts of SAP and, not least, with safety problems of the working environment due to the use of moderately thin powders which spread out in the environment.

The patent EP 0359615 A1 describes a method for applying solid dry particles of SAP on the web of wet tissue paper, prior to the drying step, and then coated with a dry web (such as tissue paper or nonwoven, etc.) and subsequently pressed and dried.

The patent EP 0437816 A1 describes a process for the production of a wet-laid nonwoven by adding SAP particles to a fiber dispersion in water or in an aqueous solution with a low alcohol content (such as methanol or ethanol) for reducing the SAP absorption capacity. By drying, the water and/or alcohol evaporate and the SAP recovers its absorption capability.

The U.S. Pat. No. 5,516,585 describes a cellulose web wherein the cellulose fibers were at least partially coated with a hot melt binder onto which, prior to the web formation and compression, solid particles of SAP were adhered.

The U.S. Pat. No. 5,607,550 describes a wet-laid nonwoven consisting of a mixture of SAP fibers and less absorbent fibers, produced by a method which involves the addition of dry SAP fibers to an aqueous dispersion of other less absorbent fibers prior to forming the web. A variant includes the preparation of a dispersion of dry SAP fibers in an organic liquid, water-miscible, in which they do not swell and then mixed, again just before the web formation, with the aqueous dispersion of the other less absorbent fibers.

The U.S. Pat. No. 5,795,439 describes a method for the production of a wet-laid nonwoven by mixing fibers and SAP in an aqueous medium under suitable conditions of low temperature, within the range from 0° C. to 25° C., which inhibits the swelling ability of the SAP. The aqueous medium can also comprise compounds inhibiting the SAP swelling, such as salts from the group NaCl, NaBr, KCl and KBr at concentrations in the range from 1 to 6% by weight.

The U.S. Pat. No. 5,997,690 describes a process for the production of a wet-laid nonwoven impregnated with SAP sensitive to ions, through a first preparation of a dispersion containing fibers and particles (having a size of less than 250 microns before use) of such a SAP. Said dispersion is then combined with a saline solution and subsequently deposited onto a filtering mesh screen belt under vacuum suction to form a web which, after washing out with water for removing the excess of salt, is finally dried.

The U.S. Pat. No. 6,056,854 describes a method for the production of a wet-laid NW wherein the fibrous structure is impregnated with SAP particles. Such a production would be based on taking advantage of the and swelling kinetics of the SAP when it is contacted with water or an aqueous solution. Said patent in fact claims the possibility to produce such materials by simply adding SAP particles to an aqueous solution of fibers and transferring such a mixture onto the mesh screen belt under vacuum suction deposition section of the wet-laid NW process machine within 5 seconds after contacting the SAP with the aqueous solution and also allowing said web to reach the drying area within 45 seconds after contacting the SAP with water.

The U.S. Pat. No. 6,979,386 describes a method for the formation of tissue paper which is performed by mixing, on the head box of the papermaking plant, a fibrous cellulose material and pre-gelatinized SAP particles (at least 30% of their absorption capability), for obtaining a cellulose web containing SAP in an amount from 0.1% to about 5% by weight, which is finally pressed and at least partially dried.

The patent US 2003/0127202 A1 describes a method for the off-line production of a composite multi-web material comprising at least two webs of tissue paper interconnected by a web of SAP fibers inserted therebetween. The SAP fibers are adhered to the inner sides of the tissue paper webs by means of an adhesive.

The patent US 2008/0115898 A1 describes an off-line method for the production of a single- or multilayer webs of tissue paper or wet-laid NW, wherein a SAP powder is distributed onto a first pre-adhered and embossed web, which can be coated, if necessary, with a second web.

The patents WO 2005098134 A1 and US 2005/0224200 A1 describe an off-line method for the production of a multi-web material wherein at least two pre-embossed webs, of which at least one is treated with a water-based adhesive, on the adhesive surface of which a layer of SAP particles is distributed prior to the lamination thereof.

WO02/100032 is directed to the production of continuous sheets formed by combining water-absorbing resin particles both of acidic and basic nature not neutralized. The production is performed by using apparatuses for producing paper, by means of wet, dry or mixed dry-wet processes, preferably with the dry airlaid process or by extrusion under thermal pressure for the wet mixing processes. The production of sheets with low specific weight, <200 g/m$^2$, with the dry airlaid process containing amounts of SAP>60% is difficult due to the tendency of the granular SAP to crumble. To overcome these drawbacks, binders, adhesives or sizing agents are used.

The materials produced by such a patent are aimed to desalting the liquids with which they are contacted in order to be converted in their salt form which render them water absorbent, whereas do not show a significant absorbing power for pure of weakly saline water.

WO03/092757 refers to the production of absorbent material sheets from suitable mixtures of SAP, a plasticizing component and other optional ingredients, which are subjected to heating and pressure, for periods, temperatures and pressures such that to avoid any reaction between the SAP and plasticizer.

It is obvious the need for developing production processes for materials with a high absorbing power and suitable mechanical strength avoiding the use of expensive off-line processes or high temperature extrusion, but which can use wet processes with known and inexpensive technologies already used for the preparation of tissue papers or wet-laid nonwovens.

SUMMARY OF THE INVENTION

The present invention suggests to using superabsorbent polymer (SAP) products in order to substantially increase the absorption capacity of paper-made or wet-laid nonwovens products.

The superabsorbent polymer (SAP) products are known for years in various applications ranging from diapers for infants and adult incontinence and for feminine hygiene to other applications of disposable products wherein the absorption of body fluids is the crucial factor.

The present invention allows to combine SAP in any form, both regular and irregular, such as granules, powders, fibers, flakes or beads, etc., with contents, entrapped within the fibrous structure of the tissue paper or wet-laid NW, up to 100%, which is, thus far, unfeasible with the current technologies, without possible secondary problems concerning the safety and with drying costs similar or slightly greater than those of the common production of paper or wet-laid nonwovens processes. Furthermore, because of the notable increase of the absorption capacity, it allows to producing and marketing products which are currently difficult or impossible to produce or which require the use of composite materials made with the off-line paper production by coupling of two or more layers of tissue papers, with only one or more layers of SAP, thereby obtaining also a benefit in terms of production/transformation costs.

Advantageously, the SAP fibers could fully replace the cellulose fibers and/or other natural, artificial and synthetic fibers.

In one aspect the present invention is directed to a method for the wet production of a superabsorbent material according to claim 1. The method contemplates the formation of an aqueous saline solution with a concentration of 0.01-4.5 N of ionic salt and pH from 0 to 6.0 or from 8.0 to 14.0 by addition of a strong acid or strong base and the dispersion in the saline solution of a water superabsorbent polymer (SAP) component selected among the polymers comprising at least one acidic resin not completely neutralized in case of acidic saline solution or comprising at least one basic resin not completely neutralized in case of basic saline solution.

The pH and salt concentration are in a relationship such that it causes a water absorption in the SAP equal to or less than about 30.00 $g_{H2O}/g_{SAP}$.

Thus, the implementation of a first web by depositing and layering under vacuum suction onto the mesh screen belt deposition of the SAP dispersion, followed by washing out of the web with a basic solution for SAP dispersions in acidic saline solutions or washing out of the web with an acidic solution for SAP dispersions in basic saline solutions for re-increasing the neutralization level of the SAP and thus the absorption capacity thereof.

Finally, a possible wash out with water of the web (for removing saline residuals) and under vacuum suction and drying up of the web.

A variant of the method contemplates the use of SAP suitably less salinized so that the same, once put in the saline solution, would produce the intended pH.

According to preferred embodiments the dispersion in the saline solution of a water superabsorbent polymer (SAP) component also includes the dispersion of natural or artificial cellulose fibers, and/or artificial or synthetic fibers, suitably made wettable with surface or in bulk treatments with surfactants, and the formation of a dispersion in aqueous saline solution of fibers and SAP at pH from 0 to 6.0 or from 8 to 14.0 depending on the type of SAP used.

According to a preferred embodiment the method contemplates the formation of subsequent multi-layers by repeating the steps of the web formation, with the same SAP and/or also preferably of a first web obtained by stratification of an anionic SAP, the stratification of a second web of cationic SAP and ultimately the final drying.

The SAP dispersed in the saline solution is preferably formed by granules, powders, fibers, flakes or pearls, individually or as mixture thereof.

The invention further contemplates the use of the absorbent material obtained according to the method of the invention for the production of paper and kitchen towels, toilet paper and facial tissues, absorbent hygiene products, such as baby and incontinent adult diapers, medical/sanitary wipes, mattress covers for beds for incontinent subjects and operating room beds, underarm liners, etc.

DETAILED DESCRIPTION

Figure 1:
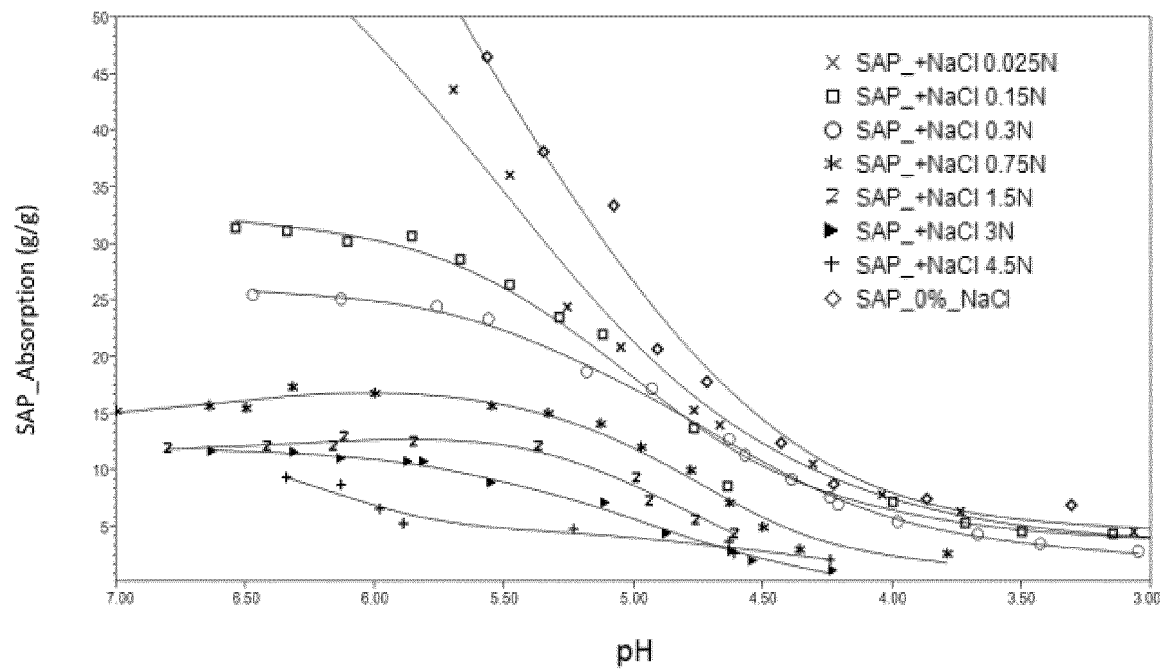
FIG. 1 is a chart depicting the absorption of $H_2O$ as g per g of SAP under different pH conditions.

The invention is based on the observation that the currently commercially available SAPs, preferably salinized at 70-80%, depending of the degree of salinization of the functional groups thereof, whether they be anionic e.g., Polyacrylates, or cationic e.g. polyvinylamines, show decreasing absorption values with the reduction of their degree of salinization until to achieve their fully acidic of basic form to a minimum of less than 2-4 $g_{H2O}/g_{SAP}$, by way of comparison, the absorption of pure cellulose is approximately 4-6 $g_{H2O}/g_{SAP}$.

Such SAPs in their fully acidic or basic form or even at different low levels of salinization can be obtained both directly starting from salinized SAP at the intended level or dispersing such commercially available materials, salinized at the current values of 70-80%, directly in the pulper or mixing tank, where the cellulose fibers disperse in water or in a saline solution at a concentration of less than 2-4% suitable for the transfer to the papermaking plant, and acidifying or basifying, depending on the type of SAP used, to the intended value of pH. In this way, the SAP is at the desired low gelatinization level and devoid of gelatinous lumps, whose formation is stopped by the saline solution and/or by pH<6 or >8 depending on the SAP used, is evenly deposited onto the under vacuum mesh screen belt deposition section of the paper machine. The dispersed mixture of fibers or particles of SAP, according to a preferred embodiment with cellulose fibers and, at the proper degree of minimum salinization, can be transferred onto the mesh screen belt under vacuum deposition section as in the normal production of paper or wet-laid nonwovens.

According to a preferred embodiment, it could be inconvenient to achieve their complete acidification or basification, whereas it would be sufficient to achieve a minimum degree of salinization leading to a such that said SAP would absorb less than 30 $g_{H2O}/g_{SAP}$ without causing the formation of a substantial gelatinized mass and thus without impairing the productivity, machinability, quality and drying costs of the tissue paper- or wet-laid NW with the SAP being combined.

The next step required for obtaining the proper SAT (Super Absorbent Tissue) material with the SAP particles having their maximum absorption capacity, involves the treatment (under suction) of the wet tissue web, containing acidic or basic particles of SAP, on the mesh screen belt formation. This step takes place onto the mesh screen belt deposition section in the interspace between the formation of the web and the transfer thereof on drying cylinders, by supplying a solution of NaOH or HCl, respectively, in order to re-salify (to the desired degree of salinization) the SAP and re-enhancing the absorbent capability thereof.

Since the gelatinization kinetics of SAPs is moderately slow relative to the re-salinization kinetics and the processing rate of the paper machine or wet-laid nonwovens machine, the SAPs do not undergone in that moment the gelatinization of remarkable amounts of water, thereby maintaining basically unchanged the drying costs.

Some kinds of plants (such as for example those TAD) for obtaining tissue papers or wet-laid NW with different compositions and different stratifications of cellulose fibers, whether they be virgin, recycled or recovered fibers, as well as for allowing high rates of the machinery, use more pulpers (each one with its particular fibrous mixture) and a simultaneously and co-lamellarly formation, through the head box, onto the under vacuum mesh screen belt. In such plants, the SAP, with or without cellulose fibers, can be put for example in a pulper in a saline solution and suitably acidified or basified depending on the nature of the SAP, whereas in another pulper cellulose fibers with NaOH or HCl at concentrations such that to neutralize the acidity or basicity, respectively, of the content of the former pulper during their coupling on the mesh screen belt deposition section—can be put. This allows to eliminate or reduce the need or the concentration of the subsequent basic or acidic treatment of re-salinization described above.

The inventors quantified the gelatinization kinetics of SAPs as a function of the pH and salinity according to the method UVAT—Under Vacuum Absorbency Test (of the SAP).

The aim of UVAT is to measuring the retention of the liquid absorbed by SAPs (Super Absorbent Polymer), at different values of pH and salinity and other conditions such as the temperature of the liquid sample and also the presence of other types of solvents such as methanol or ethanol etc., by filtration with suction under vacuum which reproduces the condition typically used in the technologies of machineries for making paper or wet-laid nonwovens.

The equipment being used consists of glass Beaker, vacuum funnel type Buchner, filter paper Ederol type 3/N, vacuum flask Erlenmeyer, vacuum pump.

The measurements were performed by means of an analytical balance with accuracy of 0.01 g, pH meter with accuracy of 0.01 pH, conductivity meter with measuring range from 0.01 µS/cm to 1000 mS/cm corresponding to an apparent salinity from 0.01 mg/l to 600 g/l KCl or 470 g/l NaCl.

(e.g. for the acidic SAP) Aqueous solutions with the following characteristics were prepared:

1. HCl solutions in water in graduated flasks of 250 ml at concentrations of 0.5-1.0-1.5-2.0-2.5-3.0-3.5-4.0-4.5 and 5.0 N for lowering the pH of the solution to be tested 2. 2N NaOH aqueous solution in a graduated flask of 100 ml for raising the pH of the non-acidified solution to be tested 3. Saline solution, for each level of salinity to be tested, of 0.00-0.025-0.05-0.10-0.15-0.30-0.75-1.50-3.0 or 4.5 N NaCl in a graduated beaker of 10 liters The method being used is as follows:

For each salinity level, a test set formed by pairs of glass beakers of 250 ml for each pH level to be tested is prepared.

To each pair of beakers, following to calibration on an analytical balance, one of the following amounts is added:

0.0-0.50-1.0-1.50-2.0-2.50-3.0-3.50-4.0-4.50-5.0-5.50-6.0-6.5-7.0-7.5-9.0-11.0-15.0-20.0 or 25.0 meq HCl or: 0.5-1.0-1.5-2.0-2.5 or 3.0 meq NaOH followed by the addition of a test saline solution until to obtain the weight of the final solution equal to 200.0 g.

To a beaker only, for each pair, 1.00 g of SAP is then added, whereas the other one will be used for rinsing during the filtration step for avoiding any change of the SAP conditions during this step.

The beaker containing the SAP is put under stirring for at least two hours in order to obtain a homogeneity of the absorption and then subjected to the measurement of the pH and conductivity, or apparent salinity, as apparent equivalence of NaCl, due to the contribution, in the conductometric measurement, of all the ions present in the solution and then to under vacuum filtration.

The contribution of the other ions, in addition to the effective NaCl added to the solution, is significant up to the normality 1.0/1.5 of NaCl used and becomes irrelevant beyond such a salinity; thus beyond the salinity 1.5N, the latter can be considered equal to the normality of NaCl being used. The net weight of the imbibed SAP thus obtained minus 1.00 g of the dry SAP used, would give the value of the absorption thereof under the measured conditions of pH and salinity.

Table 1 shows for each different NaCl concentration the absorption of $H_2O$ as g per g of SAP, wherein SAP is a superabsorbent polymer in granules obtained according to the Danson procedure, type of product DSorb A100-228 (SAP).

TABLE 1

| pH | Salinity in Normality of NaCl. | Absorption (g/g) |
|---|---|---|
| SAP__0%__NaCl | | |
| 7.37 | 0.014 | 141.18 |
| 7.23 | 0.019 | 134.46 |
| 7 | 0.022 | 116.33 |
| 6.6 | 0.024 | 90.44 |
| 6.28 | 0.028 | 81.55 |
| 6.01 | 0.030 | 63.46 |
| 5.79 | 0.033 | 53.05 |
| 5.57 | 0.036 | 46.55 |
| 5.35 | 0.038 | 38.14 |
| 5.08 | 0.042 | 33.46 |
| 4.91 | 0.044 | 20.76 |
| 4.72 | 0.045 | 17.86 |
| 4.43 | 0.048 | 12.45 |
| 4.23 | 0.050 | 8.82 |
| 3.87 | 0.054 | 7.55 |
| 3.31 | 0.060 | 7 |
| 2.82 | 0.093 | 4.98 |
| 2.46 | 0.142 | 4.48 |
| 2.24 | 0.232 | 4.05 |
| 2.03 | 0.361 | 3.91 |
| 1.91 | 0.479 | 3.72 |
| SAP__NaCl__0.025N | | |
| 6.87 | 0.051 | 66.34 |
| 6.85 | 0.054 | 64.8 |
| 6.63 | 0.057 | 60.81 |
| 6.36 | 0.059 | 56.81 |
| 6.16 | 0.063 | 52.51 |
| 5.97 | 0.065 | 49.35 |
| 5.7 | 0.067 | 43.68 |
| 5.48 | 0.070 | 36.1 |
| 5.26 | 0.071 | 24.44 |
| 5.05 | 0.074 | 20.91 |
| 4.77 | 0.077 | 15.33 |
| 4.67 | 0.079 | 14.06 |
| 4.31 | 0.082 | 10.58 |
| 4.04 | 0.084 | 7.93 |
| 3.74 | 0.088 | 6.44 |
| 3.07 | 0.102 | 4.59 |
| 2.76 | 0.124 | 3.87 |
| 2.42 | 0.172 | 3.79 |
| 2.13 | 0.268 | 3.95 |
| SAP__NaCl__0.05N | | |
| 6.84 | 0.085 | 50.27 |
| 6.69 | 0.088 | 48.97 |
| 6.48 | 0.091 | 47.54 |
| 6.16 | 0.092 | 46 |
| 5.87 | 0.097 | 44.73 |
| 5.63 | 0.098 | 40.23 |
| 5.47 | 0.101 | 33.19 |
| 5.24 | 0.103 | 32.15 |
| 5.09 | 0.105 | 23.39 |
| 5 | 0.106 | 17.98 |
| 4.83 | 0.109 | 12.44 |
| 4.48 | 0.111 | 11.95 |
| 4.28 | 0.114 | 7.61 |
| 3.94 | 0.116 | 7.03 |
| 3.38 | 0.121 | 6.41 |
| 3.05 | 0.129 | 4.68 |
| 2.73 | 0.157 | 3.77 |
| 2.42 | 0.204 | 3.4 |
| SAP__NaCl__0.1N | | |
| 6.68 | 0.151 | 40.73 |
| 6.45 | 0.152 | 39.87 |
| 6.14 | 0.154 | 39.25 |
| 5.91 | 0.156 | 36.74 |
| 5.71 | 0.159 | 32.3 |
| 5.3 | 0.160 | 31.32 |
| 4.95 | 0.164 | 30.89 |
| 4.84 | 0.165 | 24.03 |
| 4.71 | 0.167 | 23.96 |
| 4.51 | 0.169 | 19.82 |
| 4.31 | 0.172 | 15.77 |
| 4.12 | 0.171 | 12.34 |
| 4.06 | 0.174 | 7.54 |
| 3.83 | 0.175 | 6.95 |
| 3.52 | 0.181 | 5.89 |
| 3.15 | 0.186 | 5.43 |
| 2.62 | 0.21423 | 4.54 |
| SAP__NaCl__0.15N | | |
| 6.54 | 0.212 | 31.5 |
| 6.34 | 0.214 | 31.15 |
| 6.11 | 0.216 | 30.26 |
| 5.86 | 0.217 | 30.7 |
| 5.67 | 0.220 | 28.7 |
| 5.48 | 0.222 | 26.43 |
| 5.29 | 0.225 | 23.5 |
| 5.12 | 0.226 | 22.09 |
| 4.89 | 0.229 | 16.9 |
| 4.77 | 0.230 | 13.72 |
| 4.64 | 0.234 | 8.68 |
| 4.19 | 0.233 | 8.76 |
| 4 | 0.235 | 7.26 |
| 3.72 | 0.237 | 5.38 |
| 3.5 | 0.243 | 4.67 |
| 3.15 | 0.248 | 4.48 |
| 2.57 | 0.27632 | 3.78 |
| SAP__NaCl__0.3N | | |
| 6.47 | 0.384 | 25.54 |
| 6.13 | 0.384 | 25.09 |
| 5.76 | 0.386 | 24.5 |
| 5.56 | 0.386 | 23.36 |
| 5.36 | 0.390 | 22.43 |
| 5.18 | 0.390 | 18.69 |
| 4.93 | 0.393 | 17.25 |
| 4.63 | 0.397 | 12.77 |
| 4.57 | 0.397 | 11.37 |
| 4.39 | 0.397 | 9.21 |
| 4.24 | 0.402 | 7.58 |

TABLE 1-continued

| pH | Salinity in Normality of NaCl. | Absorption (g/g) |
|---|---|---|
| 4.21 | 0.401 | 6.92 |
| 3.98 | 0.405 | 5.47 |
| 3.67 | 0.405 | 4.38 |
| 3.43 | 0.410 | 3.52 |
| 3.05 | 0.413 | 2.9 |
| SAP__NaCl__0.75N | | |
| 7.14 | 0.853 | 14.48 |
| 7 | 0.853 | 15.24 |
| 6.64 | 0.854 | 15.68 |
| 6.5 | 0.846 | 15.53 |
| 6.32 | 0.849 | 17.35 |
| 6 | 0.846 | 16.83 |
| 5.55 | 0.852 | 15.73 |
| 5.33 | 0.852 | 15.03 |
| 5.13 | 0.857 | 14.15 |
| 4.97 | 0.854 | 12.06 |
| 4.78 | 0.856 | 10.02 |
| 4.63 | 0.861 | 7.16 |
| 4.5 | 0.861 | 4.98 |
| 4.36 | 0.864 | 3.09 |
| 3.79 | 0.868 | 2.68 |
| SAP__NaCl__1.5N | | |
| 7.28 | 1.459 | 11.28 |
| 6.8 | 1.486 | 11.95 |
| 6.42 | 1.501 | 12.16 |
| 6.16 | 1.497 | 12.21 |
| 6.12 | 1.497 | 13.02 |
| 5.85 | 1.476 | 12.57 |
| 5.37 | 1.478 | 12.2 |
| 5.14 | 1.472 | 10.94 |
| 4.99 | 1.485 | 9.42 |
| 4.94 | 1.476 | 7.33 |
| 4.76 | 1.482 | 5.68 |
| 4.61 | 1.478 | 4.45 |
| SAP__NaCl__3N | | |
| 6.63 | 3 | 11.7 |
| 6.31 | 3 | 11.64 |
| 6.13 | 3 | 11.03 |
| 5.87 | 3 | 10.81 |
| 5.81 | 3 | 10.78 |
| 5.55 | 3 | 8.89 |
| 5.11 | 3 | 7.17 |
| 4.87 | 3 | 4.4 |
| 4.62 | 3 | 2.86 |
| 4.54 | 3 | 2.06 |
| 4.23 | 3 | 1.19 |
| SAP__NaCl__4.5N | | |
| 9.35 | 4.5 | 13.06 |
| 8.58 | 4.5 | 12.62 |
| 6.93 | 4.5 | 11.17 |
| 6.34 | 4.5 | 9.35 |
| 6.13 | 4.5 | 8.73 |
| 5.98 | 4.5 | 6.63 |
| 5.89 | 4.5 | 5.26 |
| 5.23 | 4.5 | 4.82 |
| 4.63 | 4.5 | 3.74 |
| 4.61 | 4.5 | 2.7 |
| 4.24 | 4.5 | 2.14 |
| 4.16 | 4.5 | 1.7 |

Similarly, table 2 shows for each different NaCl concentration the absorption of $H_2O$ as g per g of SAF, wherein SAF is a superabsorbent fiber produced by Technical Absorbent type 111/6/10 (SAF).

TABLE 2

| pH | Salinity in Normality of NaCl. | Absorption g/g |
|---|---|---|
| SAF__0%__NaCl | | |
| 7.04 | 0.010 | 68.02 |
| 6.87 | 0.014 | 63.42 |
| 6.56 | 0.018 | 57.98 |
| 6.23 | 0.020 | 51.82 |
| 5.91 | 0.023 | 39.14 |
| 5.63 | 0.026 | 27.85 |
| 5.38 | 0.029 | 15.8 |
| 5.09 | 0.032 | 9.74 |
| 4.86 | 0.035 | 3.51 |
| 4.56 | 0.037 | 2.72 |
| 4.28 | 0.040 | 1.73 |
| 3.88 | 0.042 | 1.45 |
| 3.24 | 0.050 | 0.95 |
| 2.9 | 0.059 | 0.88 |
| 2.63 | 0.073 | 0.94 |
| 2.52 | 0.083 | 1.04 |
| SAF__NaCl__0.025N | | |
| 6.58 | 0.049 | 44.25 |
| 6.46 | 0.052 | 39.89 |
| 6.25 | 0.055 | 36.29 |
| 5.97 | 0.057 | 32.33 |
| 5.87 | 0.060 | 27.77 |
| 5.32 | 0.064 | 13.25 |
| 5.54 | 0.062 | 21.85 |
| 5.1 | 0.066 | 9.29 |
| 4.87 | 0.069 | 6.13 |
| 4.61 | 0.071 | 2.13 |
| 4.35 | 0.074 | 1.68 |
| 3.92 | 0.077 | 1.33 |
| 3.38 | 0.083 | 0.97 |
| 3.03 | 0.092 | 0.89 |
| SAF__NaCl__0.05N | | |
| 7.43 | 0.0863 | 31.91 |
| 7.05 | 0.085 | 32.04 |
| 6.85 | 0.084 | 32.94 |
| 6.47 | 0.083 | 34.94 |
| 6.37 | 0.085 | 32.86 |
| 6.18 | 0.087 | 30.44 |
| 5.86 | 0.090 | 26.38 |
| 5.68 | 0.092 | 20.43 |
| 5.43 | 0.094 | 16.32 |
| 5.26 | 0.096 | 12.55 |
| 5.02 | 0.099 | 6.38 |
| 4.81 | 0.102 | 2.7 |
| 4.55 | 0.104 | 1.6 |
| 4.3 | 0.107 | 1.08 |
| SAF__NaCl__0.1N | | |
| 7.66 | 0.150 | 27.59 |
| 7.21 | 0.149 | 27.74 |
| 6.87 | 0.148 | 28.62 |
| 6.75 | 0.148 | 28.52 |
| 6.39 | 0.149 | 23.77 |
| 6.14 | 0.151 | 23.78 |
| 5.9 | 0.153 | 21.37 |
| 5.65 | 0.155 | 19.37 |
| 5.45 | 0.158 | 15.9 |
| 5.24 | 0.160 | 11.5 |
| 5.06 | 0.162 | 6.77 |
| 4.85 | 0.163 | 3.52 |
| 4.65 | 0.166 | 2.95 |
| 4.44 | 0.168 | 1.32 |
| 4.18 | 0.171 | 1.25 |
| SAF__NaCl__0.15N | | |
| 7.52 | 0.207 | 26.93 |
| 7.11 | 0.207 | 27.5 |
| 6.75 | 0.204 | 24.72 |
| 6.57 | 0.204 | 25.18 |
| 6.07 | 0.210 | 21.96 |
| 5.9 | 0.208 | 20.7 |
| 5.74 | 0.211 | 18.54 |
| 5.51 | 0.213 | 16.42 |

TABLE 2-continued

| pH | Salinity in Normality of NaCl. | Absorption g/g |
|---|---|---|
| 5.33 | 0.215 | 15.87 |
| 5.15 | 0.216 | 11.11 |
| 4.97 | 0.219 | 6.72 |
| 4.79 | 0.220 | 3.82 |
| 4.57 | 0.223 | 1.75 |
| 4.34 | 0.224 | 1.19 |
| 4.07 | 0.228 | 0.87 |
| SAF_NaCl_0.3N | | |
| 7.17 | 0.3783 | 21.59 |
| 6.73 | 0.377 | 18.69 |
| 6.49 | 0.376 | 18.68 |
| 6.33 | 0.376 | 18.36 |
| 6 | 0.377 | 17.8 |
| 5.79 | 0.380 | 17.06 |
| 5.57 | 0.381 | 16.06 |
| 5.35 | 0.381 | 14.07 |
| 5.17 | 0.385 | 11.15 |
| 4.97 | 0.385 | 8.04 |
| 4.79 | 0.388 | 4.39 |
| 4.62 | 0.388 | 2.04 |
| 4.42 | 0.392 | 1.72 |
| 4.2 | 0.392 | 0.91 |
| SAF_NaCl_0.75N | | |
| 7.58 | 0.83 | 3.3 |
| 6.99 | 0.82 | 12.2 |
| 6.59 | 0.83 | 13.35 |
| 6.34 | 0.83 | 12.69 |
| 6.06 | 0.83 | 13.3 |
| 5.83 | 0.82 | 12.67 |
| 5.77 | 0.85 | 12.7 |
| 5.53 | 0.85 | 12.2 |
| 5.3 | 0.85 | 11.04 |
| 5.08 | 0.85 | 8.72 |
| 4.9 | 0.85 | 5.83 |
| 4.73 | 0.85 | 2.86 |
| 4.57 | 0.85 | 1.99 |
| SAF_NaCl_1.5N | | |
| 6.76 | 1.470 | 12.53 |
| 6.48 | 1.474 | 12.66 |
| 6.17 | 1.469 | 12.52 |
| 5.88 | 1.470 | 12.55 |
| 5.56 | 1.478 | 12.03 |
| 5.49 | 1.453 | 11.72 |
| 5.34 | 1.477 | 10.71 |
| 5.17 | 1.476 | 10.33 |
| 4.97 | 1.473 | 9.26 |
| 4.84 | 1.478 | 5.53 |
| 4.69 | 1.478 | 2.72 |
| 4.55 | 1.481 | 2.74 |
| SAF_NaCl_3N | | |
| 9.94 | 3 | 12.65 |
| 8.26 | 3 | 12.78 |
| 6.26 | 3 | 12.71 |
| 5.98 | 3 | 12.04 |
| 5.69 | 3 | 12.07 |
| 5.48 | 3 | 11.27 |
| 5.25 | 3 | 12.34 |
| 5.23 | 3 | 10.71 |
| 5.05 | 3 | 8.56 |
| 4.9 | 3 | 5.45 |
| 4.73 | 3 | 2.77 |
| 4.62 | 3 | 1.58 |
| SAF_NaCl_4.5N | | |
| 7.47 | 4.5 | 14.57 |
| 6.83 | 4.5 | 12.97 |
| 6.3 | 4.5 | 13.67 |
| 5.95 | 4.5 | 12.41 |
| 5.53 | 4.5 | 10.47 |
| 5.21 | 4.5 | 8.35 |
| 5.18 | 4.5 | 6.86 |
| 5.08 | 4.5 | 4.82 |
| 4.94 | 4.5 | 2.21 |
| 4.79 | 4.5 | 1.2 |

Figure 2:
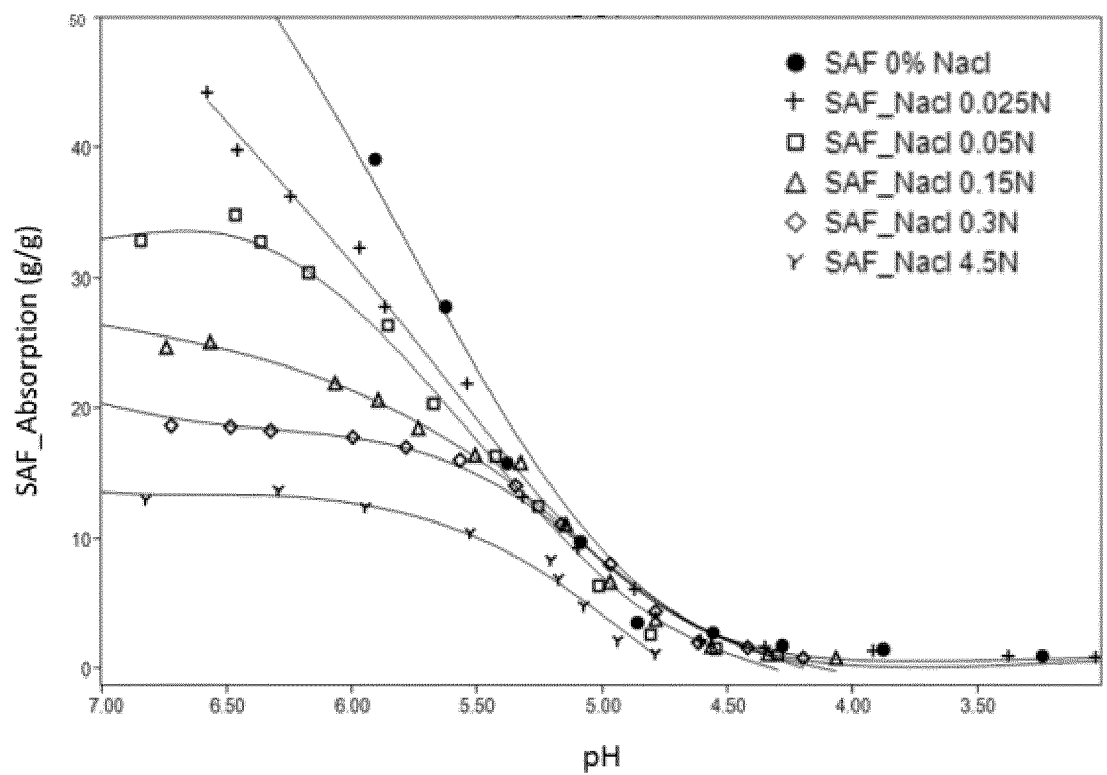
FIG. 2 is a chart depicting the absorption of $H_2O$ as g per g of SAF under different pH conditions.

FIGS. 1 and 2 show the absorption of $H_2O$ as g per g of SAP or SAF of tables 1 and 2, respectively, the lines connect and mediate the values with the same salinity according to the legend on the side. Some lines of data of the tables were omitted since considered redundant. As can be noted from these graphs, under conditions of pH less than 5.00-4.50 the water absorption in the SAP or SAF is less than 10 $g_{H2O}/g_{SAP}$ or $g_{H2O}/g_{SAF}$.

The method according to the invention uses a plant for the wet production of paper. Particularly, the method for the wet production of a superabsorbent material, comprising:

a) Formation of an aqueous saline solution with a concentration of 0.01-4.5 N of ionic salt and pH from 0 to 6.0 or from 8.00 to 14.00 by addition of a strong acid or base;

b) Dispersion in the saline solution of a water superabsorbent polymer (SAP) component selected among the polymers comprising at least one acidic resin not completely neutralized in case of acidic saline solution or comprising at least one basic resin not completely neutralized in case of basic saline solution, c) Implementation of a first web by layering and suction on the deposition canvas of the SAP dispersion.

d) Washing out of the web with a basic solution up to the partial neutralization of the acidity for SAP dispersions in acidic saline solutions or with acidic solution of the web up to the partial neutralization of the basicity for SAP dispersions in basic saline solutions;

e) Washing out of the web with water and suction;

f) Drying up of the web;

wherein the relationship between pH and salt concentration is such that it causes a water absorption in the SAP equal to or less than about 30.00 $g_{H2O}/g_{SAP}$.

As shown in FIGS. 1 and 2, under the working conditions being claimed, limited amounts of water are absorbed, despite the presence of the SAP, even at relatively high amounts, thus limiting the phenomenon of water absorption and gelatinization of the SAP. The drying costs are thus limited, and all the disadvantages, such as the intrinsic formation of bulky gelatinous lumps and the interruption of the plant, are avoided. The formation of lumps would also cause, in addition to a poor homogenization and uniformity of the cellulose wadding, long drying periods and uneconomical working rates and costs, which would prevent the implementation and the production with specific technologies of the plants for the production of paper material.

According to preferred embodiments, the method according to the invention contemplates the dispersion in the saline solution of a water superabsorbent polymer (SAP) component together with the dispersion of natural or artificial cellulose fibers, and/or artificial or synthetic fibers, suitably made wettable with surface or in bulk treatments with surfactants, and the formation of a dispersion in an aqueous saline solution of fibers and SAP at pH from 0 to 6.0 or from 8 to 14.0, based on the type of SAP used.

The SAP is selected from the group of poly-acrylic acids, a hydrolyzed acrylonitrile polymer, a hydrolyzed acrylamide polymer, a starch-acrylic acid graft copolymer, a hydrolyzed starch-acrylonitrile graft copolymer, a poly(lactic acid), a poly(aspartic acid), an ethylene-maleic anhydride copolymer, a maleic anhydride-isobutylene copolymer, a saponified vinyl acetate-acrylic ester copolymer, a sulfonated polystyrene, poly(vinylphosphoric acid), a poly(vinylphosphonic acid), a poly(vinylsulfuric acid), a poly(vinylsulfonic acid), and mixtures thereof; preferably the acidic resin is a poly-acrylic acid.

According to another embodiment of the invention, the dispersion is in a basic aqueous solution of a cationic water absorbing resin (SAP) slightly cross-linked selected from the group of a poly(vinylamine), a poly(ethylenimine), a poly(vinylguanidine), a poly(allylamine), a poly(allylguanidine), a poly(dialkylamino(meth)acrylamide), a polymer prepared from the ester analog of an N-(dialkylamino(meth) acrylamide), a poly(dimethyldialkylammonium hydroxide), a guanidine-modified polystyrene, a quaternized polystyrene, a quaternized poly(meth)acrylamide or ester analog thereof, poly(vinylalcohol-co-vinylamine), and mixtures thereof; preferably the resins are a poly(vinylamine), poly(ethylenimine), poly(vinylguanidine), poly(dimethylaminoethyl acrylamide) poly(DMAPMA).

Further webs are obtained by stratification on the web obtained from step e) by repeating the steps c)-e).

According to a further embodiment at a first web obtained by stratification of an anionic SAP, it is directly laminated a web of cationic SAP, and then subjected to a web drying step; or a repetition of anionic SAP stratification followed by cationic SAP stratification is repeated more times.

The SAP dispersed in the saline solution can consists of granules, powders, fibers, flakes or pearls, or mixtures thereof.

According to a preferred embodiment the relationship between pH and salt concentration is such that it causes a water absorption of the SAP equal to or less than about 20.00 $g_{H2O}/g_{SAP}$, preferably less than 15.00 $g_{H2O}/g_{SAP}$.

Conveniently, the method contemplates a web in which a Wet Strength resin is added, such as polyamido-amine-epichlorohydrin (PAE) resins or similar resins.

The absorbent material obtained according to the invention allows the production of paper and kitchen towels, toilet paper and facial tissues, absorbent hygiene products for babies, incontinent adults, women during or between menstruation, mattress covers for beds for incontinent subjects and operating room beds, underarm liners, layers of paper or absorbent mats for the food industry, as under food containers to absorb liquid drainage from meat, fish or vegetable, layers of absorbent paper or absorbent mats for pets or for use in coffins to absorb body fluids secreted during their decomposition and medical products to absorb exudates, for example from wounds. Other variations and modifications of the present invention would be obvious to the skilled in the field and to cover such variations and modifications is the aim of the appended claims.

The particular values and the particular settings discussed above can be changed and they are cited as mere illustration of a particular embodiment of the present invention and are not intended to limit the field of the invention.

The field of the present invention is meant to be defined by the claims appended thereto.

The invention claimed is:

1. A method for the wet production of a superabsorbent material, comprising:
   a) forming an aqueous saline solution with a concentration from 0.01 to 4.5 N of ionic salt and a pH from 0 to 6.0 by addition of a strong acid;
   b) dispersing in the saline solution a water superabsorbent polymer component (SAP) comprising at least one acidic resin not completely neutralized to form an SAP dispersion;
   c) creating a first web by layering and suction on a mesh screen belt at least a portion of the SAP dispersion;
   d) washing the first web with a basic solution to t least partially neutralize the acidity of the SAP dispersions in acid saline solution;
   e) washing the first web with water and suction; and
   f) drying the first web,
   wherein after dispersing step b), the relationship between pH and salt concentration is such that it causes a water absorption in the SAP equal to or less than 30.00 g $H_2O$/g SAP.

2. The method according to claim 1, wherein the step of dispersing the SAP in the saline solution further comprises dispersing wettable fibers selected from the group consisting of natural or artificial cellulosic fibers, and synthetic fibers, thereby forming a dispersion in aqueous saline solution of fibers and SAP at a pH from 0 to 6.0.

3. The method according to claim 1 wherein the p of the dispersion obtained in step b) ranges from 0 to 6.0 and is obtained by subjecting pre-acid SAP to levels of salinization such that once dispersed in the saline solution, it causes the desired pH conditions.

4. The method according to claim 1, wherein the SAP dispersion comprises an aqueous acid solution of an anionic water absorbing resin (SAP) lightly cross-linked and the SAP is selected from the group consisting of polyacrylic acid, a hydrolyzed acrylonitrile polymer, a hydrolyzed acrylamide copolymer, a starch-acrylic acid graft copolymer, a hydrolyzed starch-acrylonitrile graft copolymer, a poly(lactic acid), a poly(aspartic acid), an ethylene-maleic anhydride copolymer, an isobutylene-maleic anhydride copolymer, a saponified vinyl acetate-acrylic ester copolymer, a sulfonated polystyrene, a poly(vinylphosphoric acid), a poly(vinylphosphonic acid), a poly(vinylsulfuric acid), a poly(vinylsulfonic acid), and mixtures thereof.

5. The method according to claim 1, wherein steps c)-e) are repeated to obtain additional layers of webs by stratification.

6. The method according to claim 1, wherein the SAP is in the form selected from the group consisting of granules, powders, fibers, flakes or pearls, and mixtures thereof.

7. The method according to claim 1, wherein the relationship between pH and salt concentration is such that it causes a SAP water absorption of less than or equal to 20.00 g $H_2O$/g SAP.

8. A method for the wet production of a superabsorbent material, comprising:
   a) forming an aqueous saline solution with a concentration from 0.01 to 4.5 N of ionic salt and a pH from 8.0 to 14.0 by addition of a strong base;
   b) dispersing in the saline solution a water superabsorbent polymer component (SAP) comprising at least one basic resin not completely neutralized to form a SAP dispersion;
   c) creating a first web by layering and suction on a mesh screen belt at least a portion of the SAP dispersion;
   d) washing the first web with an acid solution to at least partially neutralize the basicity of the SAP dispersions in basic saline solutions;
   e) washing the first web with water and suction; and
   f) drying the first web,
   wherein after dispersing step b), the relationship between pH and salt concentration is such that it causes a water absorption in the SAP equal to or less than 30.00 g $H_2O$/g SAP.

9. The method according to claim 8, wherein the step of dispersing the SAP in the saline solution further comprises dispersing wettable fibers selected form the group consisting of natural or artificial cellulosic fibers, and/or synthetic fibers, thereby forming a dispersion in aqueous saline solution of fibers and SAP at a pH from 8 to 14.0.

10. The method according to claim 8, wherein the pH and salinization of the dispersion obtained in step b) ranges from 8.0 to 14.0 and is obtained by subjecting pre-basic SAP to levels of salinization such that once dispersed in the saline solution, it causes the desired pH conditions.

11. The method according to claim 8, wherein the SAP dispersion comprises a basic aqueous solution of a cationic water absorbing resin (SAP) lightly cross-linked and the SAP is selected from the group consisting of a poly(vinylamine), a poly(ethylenimine), a poly(vinylguanidine), a poly(allylamine), a poly(allylguanidine), a poly(dialkylamino(meth)acrylamide), a polymer prepared from the ester analog of an N-(dialkylamino(meth)acrylamide), a poly (dimethyldialkylammonium hydroxide), a guanidine-modified polystyrene, a quaternized polystyrene, a quaternized poly(meth)acrylamide or ester analog thereof, poly(vinylalcohol-co-vinylamine), and mixtures thereof.

12. The method according to claim 8, wherein steps c)-e) are repeated to obtain additional webs by stratification.

13. The method according to claim 8, wherein the form of the SAP is selected from the group consisting of granules, powders, fibers, flakes or pearls, and mixtures thereof.

14. The method according to claim 8, wherein the relationship between pH and salt concentration is such that it causes a SAP water absorption of less than or equal to 20.00 g $H_2O$/g SAP.

15. A method for the wet production of a superabsorbent material having anionic and cationic stratification webs, comprising:
   a) forming an aqueous saline solution with a concentration from 0.01 to 4.5 N of ionic salt and a pH from 0 to 6.0 or from 8.0 to 14.0 by addition of a strong acid or base;
   b) dispersing in the saline solution of a water superabsorbent polymer component (SAP) comprising at least one acidic resin not completely neutralized in case of acidic saline solution or at least one basic resin not completely neutralized in case of saline basic solution;
   c) creating a web by layering and suctioning on a mesh screen belt at least a portion of the SAP dispersion;
   d) washing the web with a basic solution to at least partially neutralize the acidity of the SAP dispersions in acid saline solutions or with an acid solution up to the desired level of neutralization of the basicity for SAP dispersions in basic saline solutions;
   e) washing the web with water and suction,
   wherein a first web obtained by repeating steps c)-e) using a SAP dispersion having a pH of from 0-6 to create an anionic SAP is directly laminated to a second web obtained by repeating steps c)-e) using a SAP dispersion having a pH of from 8-14 to create a cationic SAP, and then subjected to step;
   f) drying the combination of the first and the second web, wherein after dispersing step b), the relationship between pH and salt concentration is such that it causes a water absorption in the SAP equal to or less than 30.00 g $H_2O$/g SAP.

16. The method of claim 15, wherein the step of dispersing the SAP in the saline solution further comprises dispersing of natural or artificial cellulosic fibers, and/or synthetic fibers, thereby forming a dispersion in aqueous saline solution of fibers and SAP at pH from 0 to 6.0 or from 8 to 14.0.

17. The method of claim 15 wherein the pH of the dispersion obtained in step b) ranges from 0 to 6.0 or from 8.0 to 14.0 and is obtained by subjecting pre-acid or pre-basic SAP to levels of salinization such that once dispersed in the saline solution, it causes the desired pH conditions.

18. The method of claim 15, wherein the SAP dispersion comprises an aqueous acid solution of an anionic water absorbing resin (SAP) lightly cross-linked and the SAP is selected from the group consisting of polyacrylic acid, a hydrolyzed acrylonitrile polymer, a hydrolyzed acrylamide copolymer, a starch-acrylic acid graft copolymer, a hydrolyzed starch-acrylonitrile graft copolymer, a poly(lactic acid), a poly(aspartic acid), an ethylene-maleic anhydride copolymer, an isobutylene-maleic anhydride copolymer, a saponified vinyl acetate-acrylic ester copolymer, a sulfonated polystyrene, a poly(vinylphosphoric acid), a poly (vinylphosphonic acid), a poly(vinylsulfuric acid), a poly (vinylsulfonic acid), and mixtures thereof.

19. The method of 15, wherein the SAP dispersion comprises basic aqueous solution of the cationic water absorbing resin (SAP) lightly cross-linked and the SAP is selected from the group consisting of a poly(vinylamine), a poly(ethylenimine), a poly(vinylguanidine), a poly(allylamine), a poly(allylguanidine), a poly(dialkylamino(meth) acrylamide), a polymer prepared from the ester analog of an N-(dialkylamino(meth)acrylamide), a poly(dimethyldialkylammonium hydroxide), a guanidine-modified polystyrene, a quaternized polystyrene, a quaternized poly(meth)acrylamide or ester analog thereof, poly(vinylalcohol-co-vinylamine), and mixtures thereof.

20. The method of claim 15, wherein between step e) and f), steps c) to e) are repeated to obtain additional layers of web stratification.

21. The method of claim 20, wherein the anionic SAP stratification followed by cationic SAP stratification is repeated one or more times.

22. The method of claim 21, wherein the stratification webs include a wettable fiber selected from the group consisting of natural or artificial cellulosic fibers, and synthetic fibers, thereby forming a dispersion in aqueous saline solution of fibers and SAP at a pH from 0 to 6.0.

23. The method of claim 15, wherein the relationship between pH and salt concentration is such that it causes a SAP water absorption of less than or equal to 20.00 g $H_2O$/g SAP.

24. The method of claim 15, further comprising adding a wet strength resin in the first or second web.

25. The method of claim 24, wherein the wet strength resin is polyamido-amine-epichlorohydrin (PAE).

26. A method for the wet production of a superabsorbent material, comprising:
   a) providing an aqueous saline solution with a concentration from 0.01 to 4.5 N of ionic salt;
   b) dispersing in the saline solution a water superabsorbent polymer component (SAP) comprising at least one acidic resin not completely neutralized to form an SAP dispersion having a pH from 0 to 6.0;
   c) creating a first web by layering and suction on a mesh screen belt at least a portion of the SAP dispersion;
   d) washing the first web with a basic solution to at least partially neutralize the acidity of the SAP dispersions in saline solution;
   e) washing the first web with water and suction; and
   f) drying the first web, wherein after dispersing step b), the relationship between pH and salt concentration is such that it causes a water absorption in the SAP equal to or less than 30.00 g $H_2O$/g SAP.

27. The method of claim 26, wherein the SAP applied in step b) has a suitable degree of salinization of its functional groups such that once the SAP is dispersed in the saline solution, the pH intended for step b) is attained.

* * * * *